(12) United States Patent
Runkewitz et al.

(10) Patent No.: US 9,314,227 B2
(45) Date of Patent: Apr. 19, 2016

(54) FLEXIBLE RING PESSARY (75) Inventors: Holger Runkewitz, Leipzig (DE); Andreas Ziegner, Dresden (DE)

(73) Assignee: VivosensMedical GmbH (DE)

( * ) Notice: Subject to any disclaimer, the term of this patent is extended or adjusted under 35 U.S.C. 154(b) by 157 days.

(21) Appl. No.: 13/606,255

(22) Filed: Sep. 7, 2012

(65) Prior Publication Data
US 2013/0237771 A1 Sep. 12, 2013

(30) Foreign Application Priority Data
Sep. 9, 2011 (GB) .................................. 1115592.6

(51) Int. Cl.
A61B 10/00 (2006.01)
A61B 5/00 (2006.01)
A61F 6/08 (2006.01)
A61B 5/01 (2006.01)

(52) U.S. Cl.
CPC ............ *A61B 10/0012* (2013.01); *A61B 5/0002* (2013.01); *A61B 5/01* (2013.01); *A61B 5/4337* (2013.01); *A61B 5/6813* (2013.01); *A61F 6/08* (2013.01); *A61B 2010/0019* (2013.01)

(58) Field of Classification Search
CPC ........................................................ A61B 5/00
USPC .................... 600/300, 301, 551; 128/833, 834
See application file for complete search history.

(56) References Cited

U.S. PATENT DOCUMENTS

| | | | |
|---|---|---|---|
| 3,905,360 A * | 9/1975 | Zaffaroni ....................... | 128/833 |
| 4,111,196 A * | 9/1978 | Emmett ......................... | 128/833 |
| 4,292,965 A * | 10/1981 | Nash et al. ..................... | 128/833 |
| 4,377,157 A | 3/1983 | Zartman | |
| 4,498,481 A | 2/1985 | Lemke | |
| 4,577,640 A | 3/1986 | Hofmeister | |
| 4,677,967 A | 7/1987 | Zartman | |
| 4,753,247 A | 6/1988 | Kirsner | |
| 4,823,814 A * | 4/1989 | Drogendijk et al. .......... | 128/834 |
| 4,827,946 A * | 5/1989 | Kaali et al. ..................... | 128/830 |
| 4,888,074 A * | 12/1989 | Pocknell ........................ | 156/217 |
| 5,209,238 A | 5/1993 | Sundhar | |
| 5,224,494 A * | 7/1993 | Enhorning ..................... | 128/834 |
| 5,694,947 A * | 12/1997 | Lehtinen et al. .............. | 128/833 |
| 6,158,435 A * | 12/2000 | Dorsey ........................... | 128/830 |
| 6,189,535 B1 * | 2/2001 | Enhorning ..................... | 128/834 |
| 6,544,546 B1 * | 4/2003 | Joseph Groenewegen et al. .............................. | 424/432 |
| 6,645,137 B2 * | 11/2003 | Ulmsten et al. ................. | 600/29 |

(Continued)

FOREIGN PATENT DOCUMENTS

| | | |
|---|---|---|
| CN | 1586414 A | 3/2005 |
| DE | 3211573 A1 | 10/1983 |

(Continued)

OTHER PUBLICATIONS

Editorial, "Female Reproductive Toxicology: The Time is Now", Reproductive Toxicology, vol. 4, No. 1, pp. 1-2, 1990.

*Primary Examiner* — Rene Towa
*Assistant Examiner* — May Abouelela
(74) *Attorney, Agent, or Firm* — J.A. Lindeman & Co., PLLC (57) ABSTRACT

The present disclosure suggests an apparatus for determining at least one parameter in the vaginal channel of a user. The apparatus comprises a flexible pessary and a measurement unit comprising at least one sensor for measuring the at least one vaginal parameter. The measurement unit is reversibly mountable to the flexible pessary.

19 Claims, 4 Drawing Sheets

(56) References Cited

U.S. PATENT DOCUMENTS

| | | | |
|---|---|---|---|
| 7,005,138 B2* | 2/2006 | Mahashabde et al. | 424/434 |
| 7,036,511 B2* | 5/2006 | Nissenkorn | 128/834 |
| 7,263,999 B2* | 9/2007 | Kaseki et al. | 128/885 |
| 8,715,204 B2* | 5/2014 | Webster et al. | 600/551 |
| 2003/0083590 A1 | 5/2003 | Hochman | |
| 2005/0016545 A1* | 1/2005 | Nissenkorn | 128/834 |
| 2006/0084848 A1* | 4/2006 | Mitchnick | 600/301 |
| 2009/0266367 A1* | 10/2009 | Ziv et al. | 128/834 |
| 2010/0036208 A1* | 2/2010 | Koh et al. | 600/300 |
| 2010/0274105 A1* | 10/2010 | Rosenshein | 600/301 |
| 2012/0016258 A1* | 1/2012 | Webster et al. | 600/549 |
| 2013/0211372 A1* | 8/2013 | Rosenshein | 604/503 |

FOREIGN PATENT DOCUMENTS

| | | |
|---|---|---|
| DE | 3223657 C1 | 11/1983 |
| DE | 9215558 U1 | 1/1993 |
| DE | 4413881 A1 | 10/1995 |
| DE | 19524966 A1 | 1/1997 |
| DE | 10345282 B3 | 4/2005 |
| DE | 19943456 B4 | 10/2005 |
| EP | 0667118 A1 | 2/1995 |
| WO | 99/22680 A1 | 5/1999 |

* cited by examiner

FLEXIBLE RING PESSARY

CROSS-REFERENCE TO RELATED APPLICATION

This application claims the benefit of priority of UK patent application GB 111 55 92.6 filed on Sep. 9, 2011, the entire disclosure of which is incorporated herein by reference.

TECHNICAL FIELD

This technology relates to pessaries. In particular, the technology relates to an apparatus and a method for determining at least one parameter in the vaginal channel of a user, in particular for determining ovulation in woman.

BACKGROUND

Fertility is one of the most important health care aspects in the society. Fertility and fecundity are associated with several factors such as psychological, environmental and chemical factors. The increasing influence of environmental factors and knowledge about the associated risks to such factors are leading to a growing need for methods by which the fertility of the population can be assessed without significant encroachment of the personal circumstances of test persons. The lack of available methods for fertility screening for women is referenced in Reproduction Toxicology (1990), Vol. 4, Pages 1-2. Measurement methods for the evaluation of the menstrual cycle and fertility of women that will not encroach on their daily routines are lacking.

Determining fertility either for family planning or for contraception is a critical approach of the female health care system, and precise determination of ovulation is required. So far, some indirect methods to determine the ovulation in women are based on serum hormone levels or measurement of the basal body temperature. The method using serum hormone levels is reliable, but the wide employment of laboratory diagnostic methods that are required for these measurements (such as in urine) leads to substantial costs. Otherwise, a postovulatory rise in the temperature of about 0.5° C. (+/−0.1° C.) has been documented in the evaluation of the course of the menstrual cycle. This temperature rise is due to the circadian variations of the body core temperature amount to ±0.5° C.

DE 3223657 C2 and DE 19524966 A1 describe a measurement of the temperature with an apparatus worn on the wrist of a user. The described devices are able to save the data values and to determine ovulation. These methods and devices exhibit the following practical disadvantages: low reliability due to the disruptive influences of the ambient temperature. Additionally, these methods measure basal body temperature measured after waking-up in the morning. The experience with these methods has demonstrated a low efficacy of the data values considering the irregular daily routines of many patients.

The disruptive influences are avoided by measuring core body temperature in the vaginal canal. DE 9215558 U1 describes a device for measuring the basal body temperature in the vaginal canal which telemetrically transmits the collected data to an external memory medium.

A sensor that is connected to a processor that samples and stores the temperature data for determination of the ovulation condition is described in EP 0667118A1 and in DE 3211573A1. The basal body temperature in the vaginal canal of a user is determined and then transferred over a cable to an external memory unit.

U.S. Pat. No. 5,209,238 describes a multi-sensor for ovulation monitoring positioned in the vaginal canal and thereby allows the measurement of LH concentration, pH value and density of vaginal secretion as well as the basal body temperature. An ovulation predictor based on redox potential in vaginal secretion is described in U.S. Pat. No. 4,753,247. Likewise, U.S. Pat. No. 4,498,481 describes an electrical conductivity of vaginal secretion detector. In U.S. Pat. No. 4,827,946, a ring-formed pessary with polarized electrodes is suggested for contraception that would impede the advancement of male germs via the build-up of an electrical field.

Devices described above that can be placed in the vaginal canal (U.S. Pat. Nos. 5,209,238; 4,577,640; and 4,498,481)—although they avoid the disruptive influences—are uncomfortable for patients. Their form and size are not suitable for long-term use, because the flow of secretion is hindered in the vaginal canal. Even in short-term use, devices with inflexible casings (U.S. Pat. No. 4,827,946) or higher weight reduce wearing comfort. Measuring methods that rely on discontinuously ascertained values in urine or in breath can be error-prone if they are carried out by untrained personnel. Such methods are inherently deficient also in that the measurement interval cannot be selected to be arbitrarily small.

A medical device suggested for contraception is described in patent U.S. Pat. No. 4,292,965. This intra-vaginal ring for use as a contraceptive includes a medical layer and is placed inside the vagina for three weeks. Other intra-vaginal rings for contraception are described in U.S. Pat. No. 4,888,074 and U.S. Pat. No. 6,544,546. These intra-vaginal rings are based on the continuous release of a therapeutic agent, such as a hormone.

Patent DE 199 43 456 B4 describes a telemetric ovulation monitoring system for women that determines ovulation in a comfortable medical device to be placed in the vagina and the transmission of data values from a sensor located near where the process of ovulation occurs. This ring pessary is placed anterior to the cervix without obstructing the cervix as described. Additionally, this ring pessary includes a temperature sensor continuously transmitting data values to an external storage device.

The ring pessary described in DE 199 43 456 B4 is a device for ovulation monitoring in women in such a manner that it will be possible to reliably and confidently assess women's menstrual cycles in individual cases, as well as in routine controls, in a cost-effective manner. There is no equipment or devices that must be worn externally on the body. This ring pessary can be placed for up to 6 months. While this ring pessary works reliably over long time periods, the ring pessary changes its optical appearance over time, which is not accepted by some of the users.

The measurement system inside the ring pessary of DE 199 43 456 has to be tightly encapsulated, and the ring pessary is used as a seal. The measurement system has to be exactly positioned inside the ring pessary during the manufacturing process requiring complex, precise, and cost-intensive manufacturing, wherein high pressures are required for encapsulation. These facts increase the likelihood of damage to the ring during the manufacturing process.

SUMMARY

The claimed invention is an apparatus for determining at least one parameter in the vaginal channel of a user. The apparatus comprises a flexible pessary and a measurement unit comprising at least one sensor for measuring at least one vaginal parameter. The measurement unit is reversibly mountable to the flexible pessary. The flexible pessary ensures high comfort and a high standard in terms of microbiological quality for the user and easy insertion and removal from the vaginal channel. The reversibly mountable measurement unit makes it possible to re-use the measurement unit while the flexible pessary can be exchanged. It is also possible to replace a measurement unit while reusing the flexible pessary. The positioning of the measurement unit in the flexible pessary can be done after manufacture of the pessary and the measurement unit, which can be done in separate assembly and manufacturing steps.

The flexible pessary of the claimed invention can have a substantially annular shape, and include a measurement unit receiving section in a portion of the annular shape. For example, the flexible pessary can include a polymeric material. Further, the measurement unit receiving section can include a socket or an opening for receiving the measurement unit in the portion of the substantially annular shape. The measurement unit receiving section can include a press fit for affixing the measurement unit.

The measurement unit for determining a vaginal parameter includes at least one sensor and a housing adapted to be received in the flexible pessary with a substantially annular shape. For example, the housing can be received in a measurement unit receiving section incorporated in a portion of the substantially annual shape. The housing of the measurement unit can be a substantially rigid housing, and can include a groove with which it can be secured in the receiving section. The housing of the measurement unit can cover the sensor, a memory, a transmitter, and/or an energy source and other electronics for determining, storing, and transmitting the measured or determined parameters.

Another example embodiment of the claimed invention includes a method for determining at least one parameter in the vaginal channel of a user. The method includes mounting a measurement unit including at least one sensor to a flexible pessary; placing the flexible pessary with the measurement unit in the vagina; and determining the at least one parameter. A method of the claimed invention can also include removing the flexible pessary with the measurement unit from the vagina and removing the measurement unit from the flexible pessary.

Determining the at least one parameter can include repetitively measuring the parameter in pre-determined time intervals or continuously measuring the parameter and storing a representation of the measured parameter in a memory of the measurement unit. For example, measuring the at least one parameter in pre-determined time intervals or continuously measuring the at least one parameter can be done over at least 24 hours. The pre-determined time intervals can be in the range between about 1 minute and 20 minutes, for example, and the measured parameter can be temperature. Additionally, a method of the claimed invention can include transmitting a representation of the measured parameter from the memory of the measurement unit to a reader device for further evaluation.

BRIEF DESCRIPTION OF THE DRAWINGS

The claimed invention may be better understood when reading the detailed description of example embodiments with respect to the accompanying figures in which:

DETAILED DESCRIPTION

The claimed invention includes an apparatus for determining at least one parameter in the vaginal channel of a user. The apparatus includes a flexible pessary and a measurement unit comprising at least one sensor for measuring the at least one vaginal parameter. The measurement unit is reversibly mountable to the flexible pessary. The flexible pessary ensures high comfort and a high standard in terms of microbiological quality for the user and easy insertion and removal from the vaginal channel. The reversibly mountable measurement unit makes it possible to re-use the measurement unit while the flexible pessary can be exchanged. It is also possible to replace a measurement unit while reusing the flexible pessary. The positioning of the measurement unit in the flexible pessary can be performed after manufacture of the pessary One example embodiment of the claimed invention includes a flexible pessary that can have a substantially annular shape. The annular shape ensures safe positioning and high comfort to the user when placed in the vaginal channel. Flexible annular pessaries or ring pessaries in accordance with the claimed invention can be reversibly deformed by a user for easy and convenient placement in the vaginal channel. Insertion and removal or replacement in the vaginal channel can be done by the user, and no specific training is required. In one example embodiment of the claimed invention, a flexible pessary can include a measurement unit receiving section in a section of the substantially annular shape for receiving and holding the measurement unit.

The measurement unit receiving section can include a socket for receiving the measurement unit in a section of the substantially annular shape. The measurement unit receiving section can include an opening in the substantially annular shape, wherein the opening or hole can substantially correspond to the dimension and/or shape of the measurement unit. This allows a precise and tight position of the measurement unit in the flexible pessary.

In one example embodiment of the claimed invention, the measurement unit receiving section can be made from the flexible material of the pessary and can form a press fit for affixing the measurement unit. For example, the shape of the socket and the dimension of the opening can be somewhat smaller than the measurement unit, and the opening of the flexible pessary can be stretched around the measurement unit to fixedly hold the measurement unit in the pessary.

The socket can further include one or two lips or rims at the edges of the opening to fixedly hold the measurement unit in the opening. Alternatively, or in addition, the socket can include a rib or a raised portion that can be engaged with a groove in the housing of the measurement unit to keep the measurement unit inside the opening.

In one example embodiment of the claimed invention, the flexible pessary can be made from a polymeric material. The polymeric material can be deformable by hand and can reversibly return to its initial annular shape after deformation. The measurement unit can include a substantially rigid housing. In one example embodiment, the rigid housing protects and covers the at least one sensor and optionally an energy source, a memory, and further electronics required or desired for determining, storing and transmitting the determined parameters.

One example embodiment of the claimed invention includes a method for determining at least one parameter in the vaginal channel of a user. The method includes mounting a measurement unit comprising at least one sensor to a flexible pessary, placing the flexible pessary with the measurement unit in the vagina, and determining the at least one parameter.

After use, the flexible pessary with the measurement unit can be removed from the vagina for readout and/or for replacement. The measurement unit can be removed or detached from the flexible pessary. The separated measurement unit can be placed in a reading device, or the flexible pessary with the measurement unit can be read out.

After removal of the measurement unit from the flexible pessary, the measurement unit can be cleaned and/or inserted into a new flexible pessary for further use. No cleaning of the flexible pessary is required as a new pessary can be used each time. Cleaning of the sealed measurement unit can be easily done, and the measurement unit can be reused as long as desired.

Determining the at least one parameter can include repetitively measuring the at least one parameter in pre-determined time intervals or continuously measuring the at least one parameter and storing a representation of the measured at least one parameter in a memory of the measurement unit. The repetitive measuring or the continuous measuring can be continued as long as desired, and the parameter can be recorded over time. If the at least one parameter is the temperature, temperature curves can be determined. The repetitive measuring or the continuous measuring can be continued for at least 24 hours, and the exact basal temperature can be directly determined No estimation or evaluation is necessary. The repetitive measuring or the continuous measuring can be continued for several days, weeks, or even months, and a precise body temperature curve over one or more menstrual cycles of a woman can be determined.

Repeated measuring in intervals of about 1 minute to about 20 minutes gives sufficiently reliable temperature data. Intervals of about 5 minutes can be used.

Examples of the claimed invention will now be described in more detail. It is to be understood that the described examples and the examples shown in the figures are purely illustrative, and a person skilled in the art can modify the examples according to specific requirements. It is not necessary to implement all features shown in the examples, and a person skilled in the art can combine features shown with respect to one figure with examples shown in other figures.

FIGS. 1A-1C show an apparatus 2 from different perspectives that can be used for measuring at least one parameter inside the vaginal channel of a woman. The apparatus 2 includes a ring pessary 20 and a measurement unit 10, where the measurement unit 10 is releasably and reversibly affixed or mounted to the ring pessary 20.

The measurement unit 10 in this example embodiment includes a sensor, a transmitter unit, and an optional memory and/or energy source for measuring, storing, and transmitting at least one parameter measured in the vaginal channel. The electronic components that can be used in such a measurement unit of a ring pessary are known in the art, for example from DE 199 43 456 and DE 1030450282, the contents of which are incorporated herein by reference. The at least one parameter can include one or more of temperature, LH concentration, pH value, density of vaginal secretion, and other parameters. The apparatus 2 enables the measurement of these parameters directly in the vaginal channel. It is noted that the terms vagina and vaginal channel are used synonymously in this disclosure.

When the ring pessary 20 with the measurement unit 10 mounted to it is placed in the vaginal channel of a woman, one or more temperature measurements can be taken. The temperature measurements inside the vagina represent the actual core body temperature and are therefore much more precise than a temperature measurement taken at the skin or elsewhere in the body. The measurement unit 10 can have a memory (not shown separately) for storing a plurality of temperature measurements. This allows a continuous circadian, circa-menstrual, and/or circa-annual monitoring of the core body temperature. Continuous monitoring can include taking a temperature measurement every second, minute, or every 5, 10 or 20 minutes, or at any other time interval. The core body temperature usually alters in a time scale of minutes to hours, and measurements every minute or every 5 minutes have been shown to deliver a precise representation of the temperature changes of the core body temperature over time. The measurements can be taken 24 hours a day, seven days a week without any interruption and are only limited by readout intervals or by the lifetime of the battery in the measurement unit 10. The temperature and the time and date of the measurement and optionally additional data may be stored in the memory for later readout. This continuous measurement enables the direct measurement of the basal temperature as well as a determination of the time when the body of the user is at the basal temperature. No estimation of calculation has to be done.

The housing 11 of the measurement unit 10 is sealed and may be made from a water-tight or water-proof material. If necessary for the measurement, one or more measurement openings or windows can be provided in the housing 11. The housing 11 is made from a rigid material. For example, a ceramic materials, metals or rigid polymeric material may be used. The measurement unit 10 has no electrical connections such as wires or plugs. The measured parameters or data are transmitted via a wireless transmission to an external receiver (not shown separately). The measurement unit 10 may also contain a memory for storing the measured data and the data may be transmitted in pre-determined time-intervals. All electronic components are arranged inside the measurement unit 10.

The measurement unit 10 and the ring pessary 20 can be made from different materials and are separate elements that can be manufactured independently from each other. The measurement unit 10 and the ring pessary 20 have, however, a corresponding shape such that the measurement unit 20 can be repeatedly and reversibly mounted to and removed from the ring pessary 20. The measurement unit 10 may last for extended time periods and the maximum use time of the measurement unit 10 merely depends on the life time of the energy source. State of the art batteries allow the use of a measurement unit 10 for several months or longer.

A user may, however, want to replace the polymeric ring pessary 20 from time to time. The apparatus 2 can then be removed from the vagina, for example during bleeding. The measurement unit 10 can be easily removed from the flexible ring pessary 20 and a new ring pessary can be mounted to the measurement unit 10 to reuse and reinsert the measurement unit 10. The removal and the mounting of the measurement unit is easy to handle and can be done by the user herself. No specifically trained personnel is required.

The ring pessary 20 may be made from a flexible polymeric material to ensure safe and comfortable positioning to the user when placed anterior to the cervix without obstructing the cervix. The term flexible means that the flexible ring pessary can be deformed by hand. Deformation allows the flexible ring to be brought to a more compact form allowing convenient and easy insertion into the vaginal channel. The flexible ring pessary 20 is dimensionally stable and returns to its original annular shape after deformation. The ring pessary 20 can thus be fixed in the vaginal channel.

The ring pessary 20 does not contain any electronics, wiring or sensors.

The ring pessary 20 may additionally or optionally contain a compound or substance that is released into the vagina. This may be an additional feature that may be added when desired, but this is not required for measuring the temperature or any other parameter by the measurement unit 10. Alternatively, the ring pessary 20 may be made from a material that is not open for diffusion and cannot release any drugs or therapeutic agents.

The ring pessary 20 has a substantially annular shape 22. A section of the ring pessary 20 is formed as a reception socket 21 for receiving the measurement unit 10. Despite the reception socket 21, the ring pessary 20 has the annular shape 22 with a substantially uniform radius and thickness.

Figure 1:
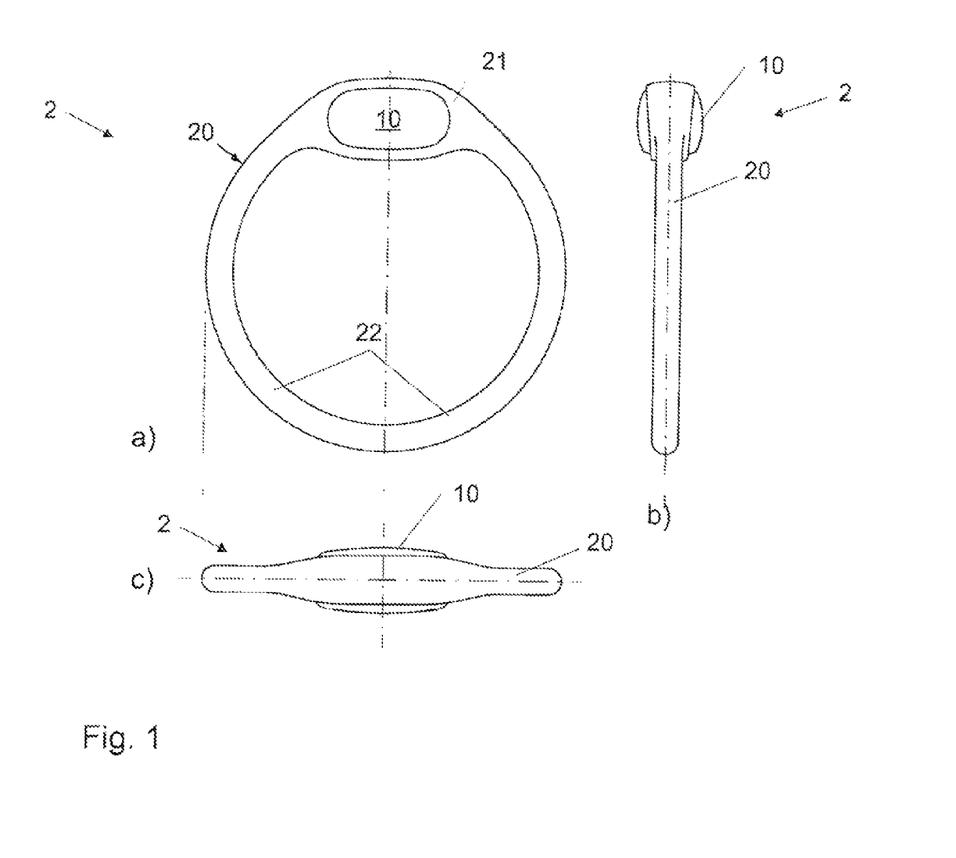
FIGS. 1A-1C show an assembled apparatus from three different perspectives.
Figure 2:
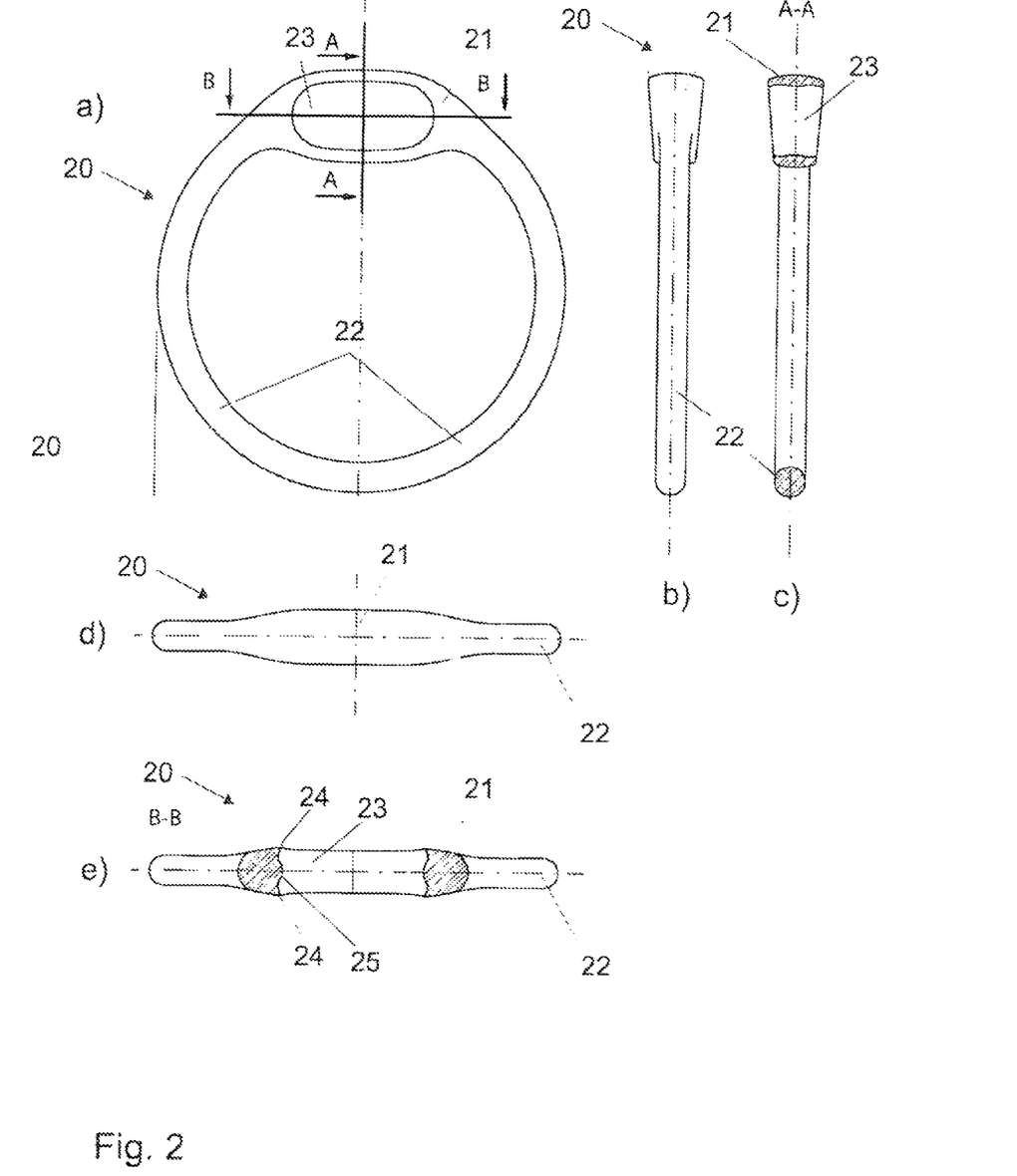
FIGS. 2A-2E e show the flexible ring pessary of FIG. 1 without measurement unit in different perspectives.

FIGS. 2A-2E show the ring pessary 20 of FIG. 1 without measurement unit 10 from different perspectives.

As shown in FIGS. 2A-2E, the ring pessary 20 has a substantially annular form 22 and a measurement unit receiving section. The measurement unit receiving section includes a reception socket 21 for the measurement unit 10 and is designed to position and fixedly support and hold the measurement unit 10 in place. The reception socket 21 includes an opening 23 in the ring pessary 20. The opening 23 corresponds substantially to the shape and dimension of the measurement unit 10. In this way the ring pessary 20 and the measurement unit 10 can be manufactured separately and can be assembled easily. No specific technical skills are required.

The dimensions of the opening 23 may, however, be chosen to be somewhat smaller than the dimensions of the measurement unit 10 to hold the measurement unit 10 tightly in the flexible ring pessary 20. Flexible material may be used for clamping the measurement unit 10 in the socket opening 23. The reception socket 21 may further include a lip 24 at one or both sides forming an edge of the opening 23. The lips 24 are made from the flexible material of the ring pessary and are integrally formed. The lips 24 may be used to fixedly hold the measurement unit 10. In the example shown, no specific fixation means such as screws, glue or the like are necessary. However, different ways to fix the measurement unit 10 to the ring pessary 20 may be employed. In addition or alternatively to the lips 24, a ridge 25 or rib is provided in the opening 23. The ridge 25 can engage with a corresponding groove 12 in the measurement unit 10, when the measurement unit 10 is affixed to the ring pessary 20. The ridge 25 is made from the flexible material and is integrally formed in the ring pessary 20.

The pessary ring 20 and the measurement unit 10 have a substantially crack-free, edge-free and corner-free shape. This ensures wearing comfort for the user and can avoid infectious agents like bacteria or fungus.

The ring pessary 20 shown in the Figures is integrally formed from a single piece made from one material. For example, a polymeric material may be used. For example, at least one of rubber, latex, LDPE (low density polyethylene) and/or an ethylene-vinyl acetate-copolymer or others can be used. Combinations of these materials and other similar materials can also be used. As one example, a polymeric material sold under the trademark "FLEXAREN" by Innospec Leuna GmbH of Leuna, Germany may be used as polymeric material ethylene-vinyl acetate-copolymer. A copolymer having an ethylene-vinyl acetate portion of about 1 to 40%, or preferably of about 10 to 25% can be used. The flexible material can have a hardness of Shore type A of about 75 to 90, in particular about 82 to 87, and of Shore type D of about 20 to 40 in particular of about 25 to 35. The flexible material can have a tensile strength of about 5 to 15 MPa, for example 10 MPa. The above parameters have been found to provide and optimize easy and safe positioning of the pessary and a safe, but releasable fixation of the measurement unit 10 in the pessary 20. Other flexible materials with different or similar properties, however, may be used allowing a reversible deformation of the ring pessary 20 into a compact shape allowing easy insertion/removal in the vaginal channel. The flexibility increases the wearing comfort for the user. Furthermore, the flexibility of the material allows removably attaching and securing the measurement unit 10 to the reception section of the ring pessary 20. The material should be dimensionally stable and recover its original annular shape after deformation. The flexible material does not contain any electronics, batteries or the like, which are all arranged in the measurement unit 10.

The ring pessary 20 may have a diameter of 50 to 60 mm, and the thickness of the ring parameter may be in the range of a few millimeters.

FIGS. 3A-3D show the measurement unit 10 removed from the apparatus 2 of FIG. 1. The measurement unit 10 includes a rigid housing 11 in which sensors and electronics are arranged. For example, one or more temperature sensors, a memory, a controller, an energy source (battery), and a radio frequency transmitter or transceiver are arranged and sealed inside the measurement unit 10. The rigid housing 11 is made from a rigid material, as for example ceramics, metals, or rigid polymeric material. The rigid measurement unit 10 is sealed and can protect the electronics and the battery from the body of the user and vice versa.

Figure 3:
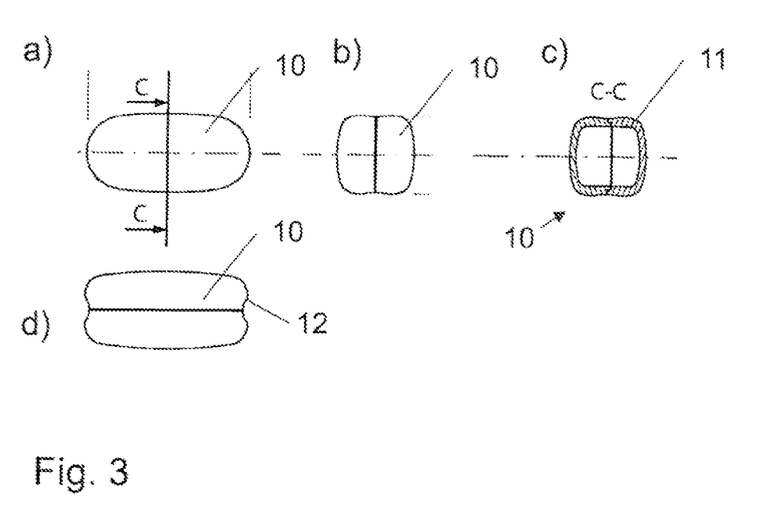
FIGS. 3A-3D show the measurement unit removed from the apparatus.
Figure 4:
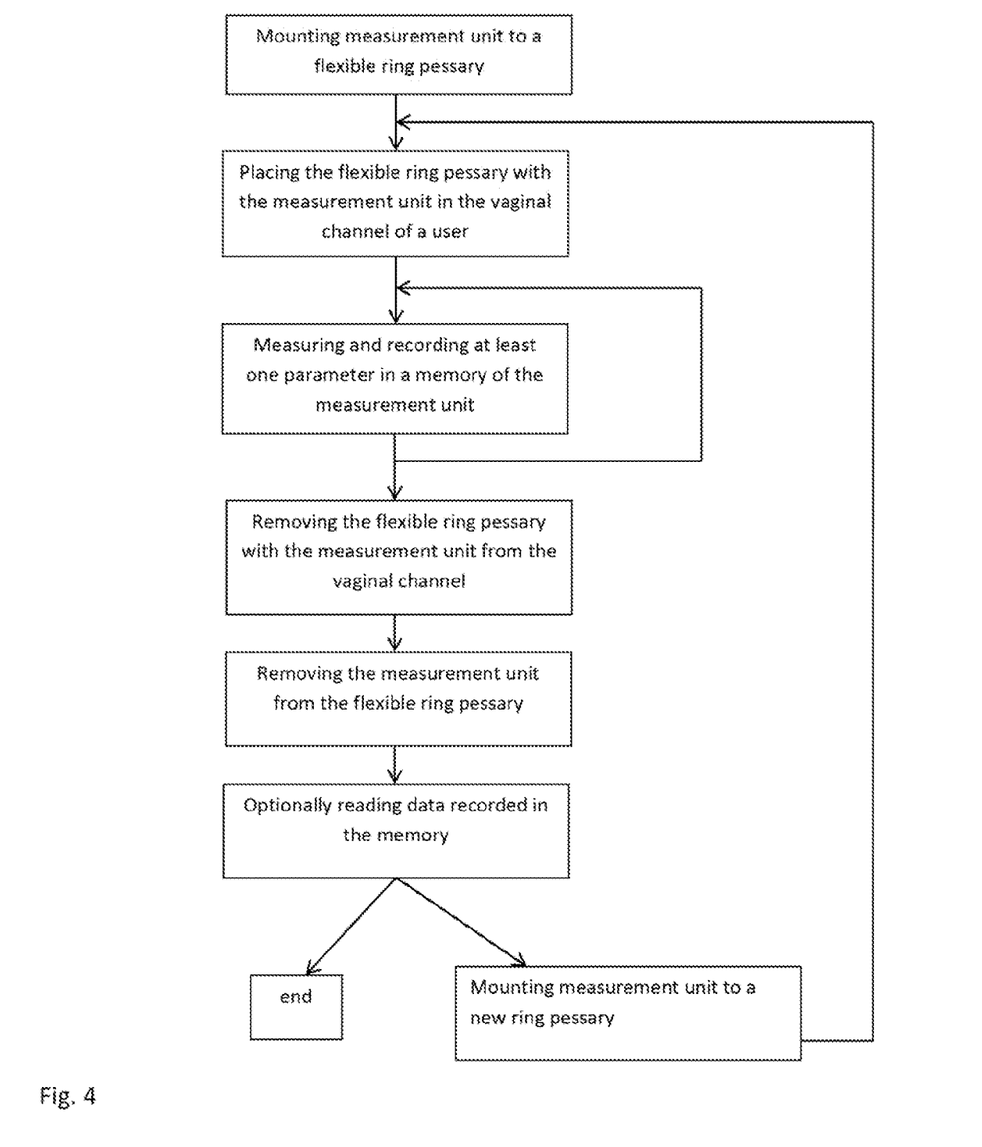
FIG. 4 shows a flow chart of a method for determining a parameter in the vaginal channel of a user in accordance with the claimed invention.

As shown in FIG. 3D, for example, the rigid housing 11 of the measurement unit 10 comprises a groove 12. The groove 12 may come into mutual contact with the ridge 25 of the ring pessary 20 when the measurement unit 10 is mounted to the ring pessary 20.

The apparatus 2 described above may be advantageously used over a long time period, wherein the ring pessary 20 is replaced from time to time while the measurement unit 10 can be reused for a longer time period. For example, the ring pessary 20 can be exchanged during or after the bleeding of menstruation. In this way, the measurement unit 10 can be used over a longer period while keeping the system hygienic and user friendly.

Data comprising representations of the parameters measured by and stored in the memory of the measurement unit 10 may be read when the measurement unit 10 is removed from the vagina. The measurement unit 10 can be removed from the flexible pessary 20, and the measurement unit 10 may be placed in, or in proximity of, a reader for transmission of data stored in the memory of the measurement unit 10 to the reader. In one example embodiment, the measurement unit 10 remains in the pessary during transmission of the data. In another example embodiment, the flexible pessary with the measurement unit may remain in the vagina when transmitting the data to a reader. Reading out the data may comprise radio frequency transmission from the measurement unit 10 to the reader.

It is also possible to maintain the ring pessary 20 and to exchange the measurement unit 10 by a different measurement unit, for example if different parameters are to be measured or if maintenance of the measurement unit 10 is required.

The apparatus 2 also enables safe, simple, and easy positioning of the measurement device 10 in the ring pessary 20.

The positioning is also cost efficient as there is no need to place the measurement unit 10 inside the polymeric material of the ring pessary 20.

A person skilled in the art will understand that one or more features of the above examples can be omitted when implementing the claimed invention. The person skilled in the art will also adapt the disclosure to other needs, and other measurement units 10 can be provided. It is also possible to use a drug dispensing system instead of, or in addition to, the measurement unit and/or to use a replaceable drug dispensing system instead of the measurement unit. An electronically controlled drug release system can also be implemented in the pessary of the claimed invention.

The claimed invention is:

1. An apparatus for determining at least one parameter in a vaginal channel, the apparatus comprising:
   a flexible pessary; and
   a removable measurement unit comprising a housing, at least one sensor, and a transmitter unit, wherein the at least one sensor and the transmitter unit are arranged inside and enclosed by the housing of the removable measurement unit,
   wherein the housing of the measurement unit is reversibly mountable to the flexible pessary; and
   wherein the flexible pessary is reversibly deformable.

2. The apparatus of claim 1, wherein the flexible pessary has a substantially annular shape and comprises a measurement unit receiving section in a portion of the substantially annular shape.

3. The apparatus of claim 2, wherein the measurement unit receiving section comprises a socket configured to receive the removable measurement unit in the portion of the substantially annular shape.

4. The apparatus of claim 2, wherein the measurement unit receiving section comprises an opening in the substantially annular shape, wherein the opening corresponds substantially to the shape of the removable measurement unit.

5. The apparatus of claim 2, wherein the measurement unit receiving section and the removable measurement unit form a press fit.

6. The apparatus of claim 1, wherein the flexible pessary comprises a polymeric material.

7. The apparatus of claim 1, wherein the removable measurement unit comprises a substantially rigid housing.

8. The apparatus of claim 1, wherein the at least one sensor is a temperature sensor.

9. The apparatus of claim 1, wherein the sensor, the transmitter unit, a memory, and an energy source are arranged inside the removable measurement unit.

10. The apparatus of claim 1, wherein the removable measurement unit further comprises a memory.

11. The apparatus of claim 1, wherein the housing of the removable measurement unit is sealed.

12. The apparatus of claim 1, wherein the flexible pessary does not include a sensor, a transmitter unit, a memory, or an energy source.

13. An apparatus for determining at least one parameter in a vaginal channel, the apparatus comprising:
    a removable measurement unit comprising at least one sensor and a transmitter unit in a rigid and sealed housing; and
    an annular pessary, made from a reversibly deformable flexible material and comprising a rigid and sealed housing receiving section,
    wherein the removable measurement unit is reversibly mountable to the annular pessary.

14. A method for determining at least one parameter in the vaginal channel of a user, the method comprising:
    mounting a removable measurement unit comprising at least one sensor and at least one transmitter unit in a sealed housing to a reversibly deformable flexible pessary;
    placing the flexible pessary with the removable measurement unit in the vagina;
    determining the at least one parameter;
    removing the flexible pessary with the removable measurement unit from the vagina; and
    removing the removable measurement unit from the flexible pessary.

15. The method of claim 14, wherein determining the at least one parameter comprises repetitively measuring the at least one parameter in pre-determined time intervals or continuously measuring the at least one parameter and storing a representation of the measured at least one parameter in a memory of the removable measurement unit.

16. The method of claim 15, wherein measuring the at least one parameter in pre-determined time intervals or continuously measuring the at least one parameter is done over at least 24 hours.

17. The method of claim 15, wherein the pre-determined time intervals are in the range between about 1 minute and 20 minutes.

18. The method of claim 14, wherein the at least one parameter is a temperature.

19. The method of claim 15, further comprising:
    transmitting the representation of the at least one parameter from the memory of the removable measurement unit to a reader device for further evaluation.

* * * * *